US009655586B2

(12) United States Patent
Yagi et al.

(10) Patent No.: US 9,655,586 B2
(45) Date of Patent: May 23, 2017

(54) RADIATION IMAGING APPARATUS AND RADIATION IMAGING SYSTEM

(71) Applicant: CANON KABUSHIKI KAISHA, Tokyo (JP)

(72) Inventors: Tomoyuki Yagi, Honjo (JP); Toshio Kameshima, Kumagaya (JP); Katsuro Takenaka, Honjo (JP); Atsushi Iwashita, Saitama (JP); Eriko Sato, Tokyo (JP); Hideyuki Okada, Honjo (JP); Takuya Ryu, Kokubunji (JP); Kosuke Terui, Honjo (JP)

(73) Assignee: Canon Kabushiki Kaisha, Tokyo (JP)

( * ) Notice: Subject to any disclaimer, the term of this patent is extended or adjusted under 35 U.S.C. 154(b) by 139 days.

(21) Appl. No.: 14/797,391

(22) Filed: Jul. 13, 2015

(65) Prior Publication Data
US 2016/0015358 A1  Jan. 21, 2016

(30) Foreign Application Priority Data

Jul. 17, 2014 (JP) .................................. 2014-146763

(51) Int. Cl.
| H05G 1/56 | (2006.01) |
| A61B 6/00 | (2006.01) |
| G01T 1/17 | (2006.01) |
| H03F 3/45 | (2006.01) |
| H03F 3/70 | (2006.01) |
| H04N 5/32 | (2006.01) |

(Continued)

(52) U.S. Cl.
CPC ............ A61B 6/585 (2013.01); A61B 6/4266 (2013.01); G01T 1/17 (2013.01); H03F 3/45475 (2013.01); H03F 3/70 (2013.01); H04N 5/32 (2013.01); H04N 5/355 (2013.01); H04N 5/378 (2013.01); *H03F 2203/45514* (2013.01); *H03F 2203/45634* (2013.01)

(58) Field of Classification Search
CPC ........ G01N 23/00; G01N 23/04; G01N 23/06; G01N 23/063; G01N 23/08; G01N 23/083; A61B 6/00; A61B 6/54; A61B 6/585; A61B 6/4266; A61B 6/4233; G01T 1/2928; G01T 1/17; H03F 3/68; H03F 2200/261; H05G 1/56
USPC ...... 378/62, 98.8, 114, 115, 116; 250/370.09
See application file for complete search history.

(56) References Cited

U.S. PATENT DOCUMENTS

| 7,403,594 B2 | 7/2008 | Endo et al. |
| 7,645,995 B2 | 1/2010 | Yagi et al. |

(Continued)

FOREIGN PATENT DOCUMENTS

JP          2004-85383 A      3/2004

*Primary Examiner* — Jurie Yun
(74) *Attorney, Agent, or Firm* — Fitzpatrick, Cella, Harper & Scinto (57) ABSTRACT

Provided is a radiation imaging apparatus, including: a first conversion element arranged to convert a radiation ray into electric charge in order to obtain a radiographic image; a first amplifier arranged to output a voltage corresponding to the electric charge of the first conversion element; a second conversion element arranged to convert the radiation ray into electric charge in order to detect radiation irradiation; a second amplifier arranged to output a voltage corresponding to the electric charge of the second conversion element; and a control circuit configured to control the first amplifier and the second amplifier, in which the control circuit is capable of controlling the second amplifier independently of control that is exerted over the first amplifier.

9 Claims, 7 Drawing Sheets

(51) Int. Cl.
*H04N 5/355* (2011.01)
*H04N 5/378* (2011.01)

(56) References Cited

U.S. PATENT DOCUMENTS

| | | |
|---|---|---|
| 7,839,977 B2 | 11/2010 | Kameshima et al. |
| 7,880,145 B2 | 2/2011 | Yagi et al. |
| 7,965,817 B2 | 6/2011 | Kameshima et al. |
| 2014/0112448 A1 | 4/2014 | Takenaka et al. |
| 2014/0285689 A1 | 9/2014 | Ryu et al. |
| 2014/0361189 A1 | 12/2014 | Kameshima et al. |

RADIATION IMAGING APPARATUS AND RADIATION IMAGING SYSTEM

BACKGROUND OF THE INVENTION

Field of the Invention

The present invention relates to a radiation imaging apparatus and a radiation imaging system.

Description of the Related Art

In medical and other fields, there have been put into practical use radiation imaging apparatuses, which are configured to receive irradiation of a radiation ray or the like after being transmitted through a subject, hold image signals of the subject's image, and output electric charge signals that reflect the held radiographic image. As an example of the radiation imaging apparatuses, there is given one that is configured to combine a photo sensor with a semiconductor material or a fluorescent substance that generates electric charge in an amount determined by the amount of radiation irradiating the apparatus. This radiation imaging apparatus has an area sensor unit, which includes thin film transistor (TFT) switches and photoelectric conversion elements. The TFT switches are formed mainly of amorphous silicon on a glass substrate in a two-dimensional pattern. The photoelectric conversion elements convert a radiation ray into electric charge. The radiation imaging apparatus switches the operation of the area sensor unit in synchronization with a control signal, which is input via an I/O device connected to the radiation imaging apparatus.

Introducing this type of radiation imaging apparatus requires, unlike film-type radiation imaging apparatuses, which are older technology, connecting the radiation imaging apparatus via an I/O device to a radiation generating apparatus and a control system that are located in a hospital. The I/O device varies from maker to maker, which means that an alteration to equipment to be connected to the I/O device and, in some cases, even replacement of the whole radiation generating apparatus, are necessary. The introduction cost is therefore problematically high.

In the radiation imaging apparatus, the gain of a column amplifier is set based on a predicted imaging dose range, the pixel sensitivity, and the noise of a readout circuit. However, a preset amplification ratio may not work depending on the performance of the radiation imaging apparatus and the positional relation between a subject and the radiation imaging apparatus. Specifically, there are cases where the positional relation of a subject with the radiation imaging apparatus makes the dose of the incident radiation ray unexpectedly large and where a radiation ray transmitted through a thick subject falls farther short of the radiation imaging apparatus than expected. In such cases, the excessively large dose or the excessively small dose can degrade image quality in an area that needs diagnosis most (an interested area).

Accordingly, using the radiation imaging apparatus involves such work as modifying the length of radiation irradiation time empirically by taking radiation conditions and the positional relation with the subject into consideration, and listing several hundred combinations of radiation conditions to register the conditions in advance, which are heavy burden to a user of the radiation imaging apparatus.

A radiation detecting apparatus described in Japanese Patent Application Laid-Open No. 2004-85383 is provided with pixels for detecting the X-ray irradiation amount aside from pixels for forming an image. X-ray irradiation can be detected by monitoring the dose of an X-ray that irradiates a sensor with the use of these detecting pixels. This technology eliminates the need for a work of connecting an I/O device to an X-ray generating apparatus when the radiation detecting apparatus is introduced to a hospital, thereby reducing the introduction cost. The radiation detecting apparatus capable of constant monitoring of the X-ray dose can also be applied to automatic exposure control (AEC) of the X-ray irradiation amount in which a session of X-ray irradiation is monitored to stop X-ray irradiation when the right X-ray dose is reached.

However, the radiation detecting apparatus of Japanese Patent Application Laid-Open No. 2004-85383, where signals of the X-ray irradiation amount detecting pixels are read out by a shared readout circuit, which reads out signals of the image forming pixels as well, has the following problems:

The first problem is power consumption. When performing a readout operation, the readout circuit consumes a very large amount of current in order to reduce the noise of the readout circuit itself. Detecting X-ray irradiation involves constant readout of the X-ray irradiation amount detecting pixels, which means that a huge amount of power is consumed to obtain one X-ray image. An increase in power consumption gives rise to problems such as limitations put on the length of drive time by heat generation of equipment, and a shortened drive time in a battery-driven radiation imaging apparatus.

The second problem is the time required to output data. The readout circuit, which is designed so as to be capable of reading out a plurality of pixel columns, has a multiplexer therein to select signals sent from pixel columns sequentially and transfer the selected signals to the outside of the readout circuit. The radiation detecting apparatus of Japanese Patent Application Laid-Open No. 2004-85383 takes time to estimate the X-ray dose because the readout of the X-ray irradiation amount detecting pixels for the purpose of X-ray dose detection is accompanied by the readout of the other pixels, i.e., the image forming pixels. In the case of the short irradiation of an intense X-ray, lengthy readout of the detecting pixels means that the right X-ray dose has been exceeded by the time a control circuit determines that there has been X-ray irradiation, and therefore hinders proper control by AEC.

SUMMARY OF THE INVENTION

The present invention provides a radiation imaging apparatus and a radiation imaging system, which are capable of reducing power consumption or cutting short the time required to detect radiation.

According to one embodiment of the present invention, there is provided a radiation imaging apparatus, including: a first conversion element arranged to convert a radiation ray into electric charge in order to obtain a radiographic image; a first amplifier arranged to output a voltage corresponding to the electric charge of the first conversion element; a second conversion element arranged to convert the radiation ray into electric charge in order to detect radiation irradiation; a second amplifier arranged to output a voltage corresponding to the electric charge of the second conversion element; and a control circuit configured to control the first amplifier and the second amplifier, in which the control circuit is capable of controlling the second amplifier independently of control that is exerted over the first amplifier.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

First Embodiment

Figure 1:
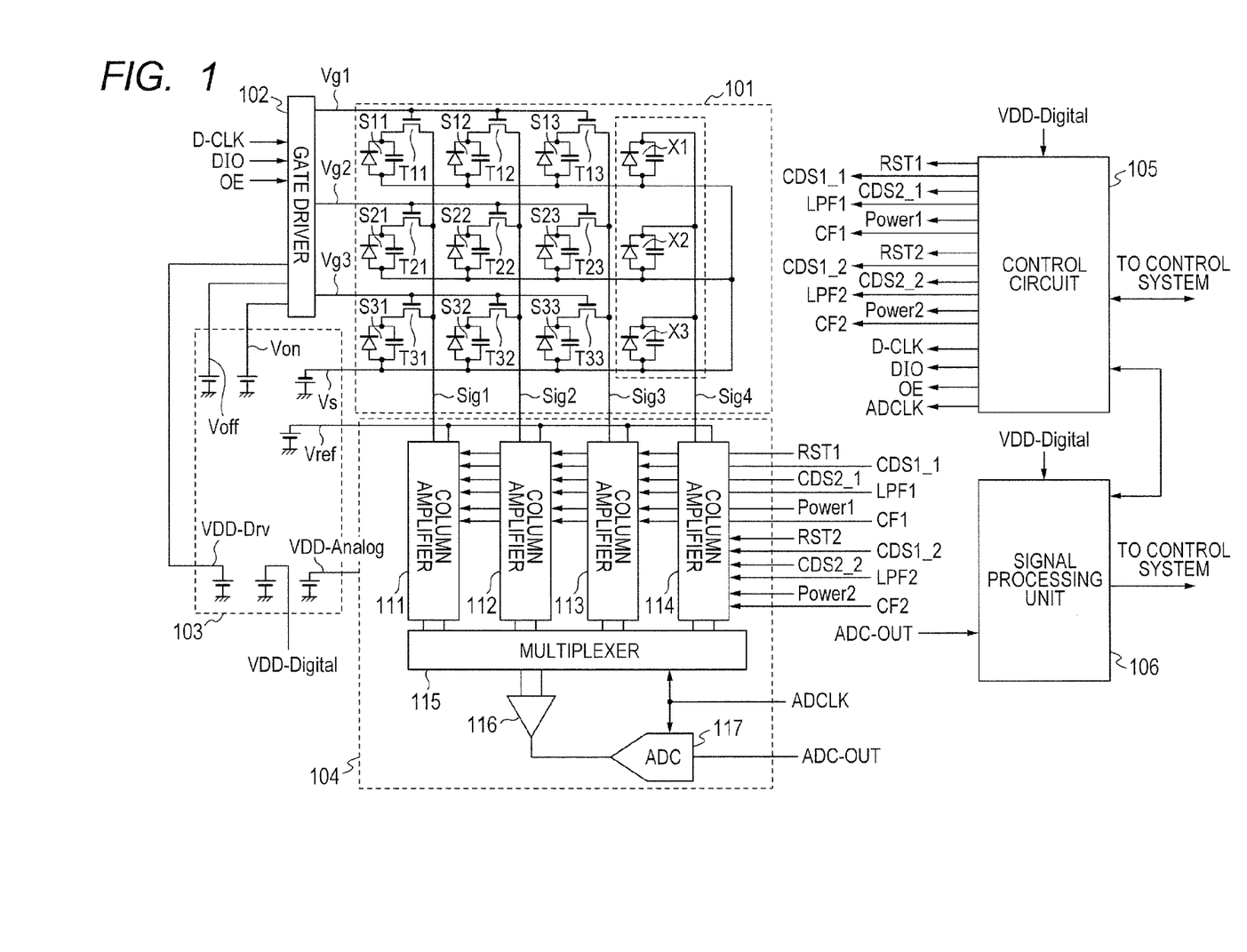
FIG. 1 is a diagram for illustrating a configuration example of a radiation imaging apparatus.

FIG. 1 is a diagram for illustrating a configuration example of a radiation imaging apparatus according to a first embodiment of the present invention. An area sensor 101 includes first conversion elements S11 to S33, second conversion elements X1 to X3, and TFT switches T11 to T33. The first conversion elements S11 to S33 and the TFT switches T11 to T33 are included in a plurality of image pixels for obtaining a radiographic image. The second conversion elements X1 to X3 are included in a plurality of radiation detecting pixels for detecting radiation irradiation in order to monitor the radiation irradiation amount, or the like. The conversion elements S11 to S33 and X1 to X3 are arranged so as to together form a matrix pattern. The conversion elements S11 to S33 and X1 to X3 convert a radiation ray (for example, X-ray) into electric charge. For instance, the conversion elements S11 to S33 and X1 to X3 each include a wavelength conversion member, which is made of GOS or CsI and converts a radiation ray (X-ray) into light, and a photodiode, which converts light into electric charge. Alternatively, the conversion elements S11 to S33 and X1 to X3 may each be an element that converts a radiation ray directly into an electric charge. Gate lines Vg1 to Vg3 supply gate pulses to gates of the TFT switches T11 to T33. The TFT switches T11 to T33 are each connected between one of the conversion elements S11 to S33 and one of column amplifiers 111 to 113. Signal lines Sig1 to Sig3 transfer electric charge that are accumulated in the conversion elements S11 to S33 to the column amplifiers 111 to 113. A signal line Sig4 transfers electric charge that are accumulated in the conversion elements X1 to X3 to a column amplifier 114. A line for a sensor bias voltage Vs supplies a voltage necessary for photoelectric conversion to the conversion elements S11 to S33 and X1 to X3. A gate driver 102 outputs gate pulses to the gate lines Vg1 to Vg3 to turn on/off the TFT switches T11 to T33 row by row at arbitrary timing.

A readout circuit 104 is connected to the signal lines Sig1 to Sig4. The readout circuit 104 converts electric charge of the signal lines Sig1 to Sig4 into a voltage, holds the voltage, converts the held voltage into a digital signal, and outputs the digital signal. The readout circuit 104 includes the column amplifiers 111 to 114, a multiplexer 115, a sample-and-hold amplifier 116, and an analog/digital converter 117. The column amplifiers 111 to 114 are connected to the signal lines Sig1 to Sig4, respectively. The column amplifiers 111 to 113, which are first column amplifiers, are arranged side by side in the row direction so as to be connected to the first conversion elements S11 to S33, which are aligned in the column direction. The first column amplifiers 111 to 113 output voltages corresponding to electric charge of the first conversion elements S11 to S33. The column amplifier 114, which is a second column amplifier, is connected directly to the second conversion elements X1 to X3, and outputs a voltage corresponding to electric charge of the second conversion elements X1 to X3. The multiplexer 115 outputs signals from the column amplifiers 111 to 114 to a downstream circuit in time series. The sample-and-hold amplifier 116 outputs a differential between signals from the multiplexer 115 to the analog/digital converter 117. The analog/digital converter 117 converts analog signals that are output from the sample-and-hold amplifier 116 into digital signals.

A control circuit 105 uses control signals to drive the gate driver 102 and the readout circuit 104. A power circuit 103 supplies a supply voltage necessary to the readout circuit 104, the gate driver 102, and the area sensor 101.

The column amplifier 114 connected to the conversion elements X1 to X3 can be controlled independently of the other column amplifiers 111 to 113. The control circuit 105 outputs controls signals RST1, CDS1_1, CDS2_1, LPF1, Power1, and CF1, which are for the column amplifiers 111 to 113, and control signals RST2, CDS1_2, CDS2_2, LPF2, Power2, and CF2, which are for the column amplifier 114. The control circuit 105 controls the column amplifiers 111 to 114.

Figure 2:
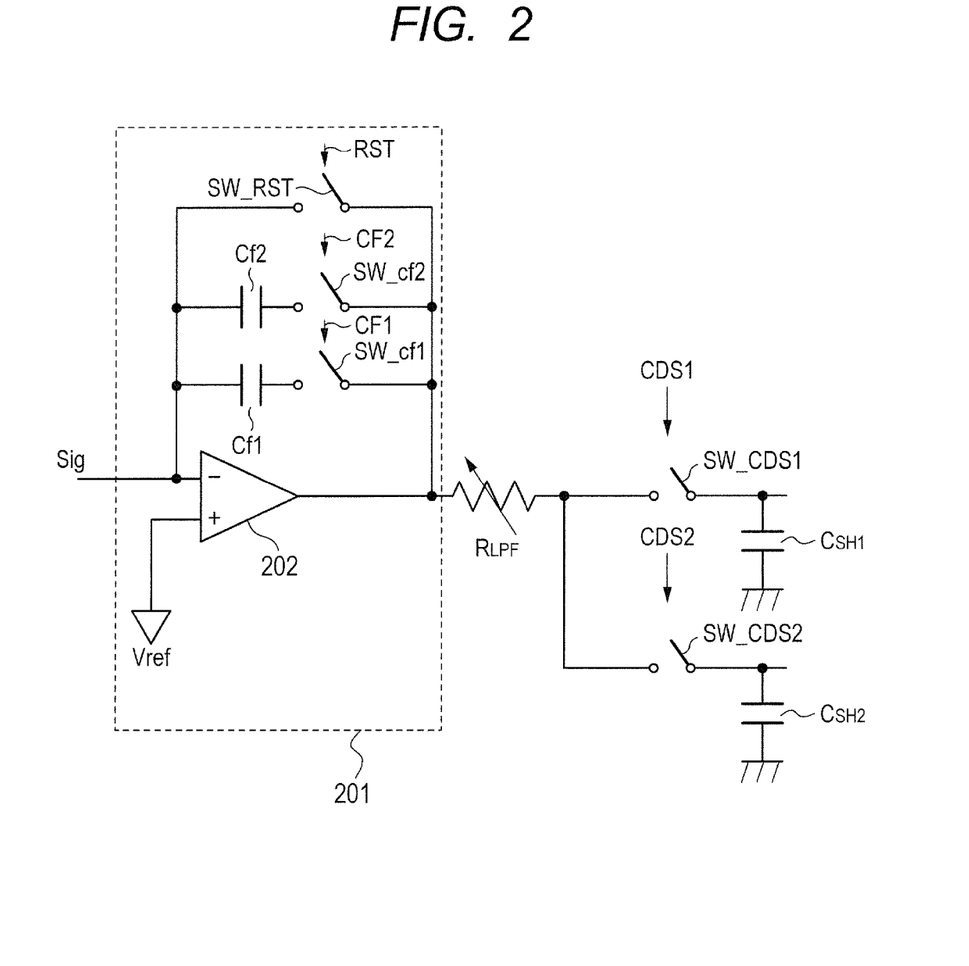
FIG. 2 is a diagram for illustrating a configuration example of a column amplifier.

FIG. 2 is a diagram for illustrating an example of the configuration that the column amplifiers 111 to 114 in FIG. 1 each have. The column amplifiers 111 to 114 each include an integrating amplifier 201, a resistor $R_{LPF}$, which is connected to an output terminal of the integrating amplifier 201, switches SW_CDS1 and SW_CDS2, and capacitors $C_{SH1}$ and $C_{SH2}$. The switch SW_CDS1 and the capacitor $C_{SH1}$ form a sample-and-hold circuit. The switch SW_CDS2 and the capacitor $C_{SH2}$ form another sample-and-hold circuit.

The integrating amplifier 201 has a negative input terminal, which is connected to a signal line Sig, and a positive input terminal, which is connected to a node of a reference voltage Vref. The signal line Sig is one of the signal lines Sig1 to Sig4 in FIG. 1. A serial connection circuit that connects a feedback capacitor Cf1 and a switch SW_cf1 in series, a serial connection circuit that connects a feedback capacitor Cf2 and a switch SW_cf2 in series, and a switch SW_RST are connected between the output terminal of the integrating amplifier 201 and the signal line Sig. The switch SW_RST is capable of short-circuiting the ends of the feedback capacitor Cf1 and the ends of the feedback capacitor Cf2.

The integrating amplifier 201 uses the feedback capacitors Cf1 and Cf2 to accumulate electric charge of the signal line Sig, converts the electric charge into a voltage, and outputs the voltage. The gain of the integrating amplifier 201 is determined by the connection to the feedback capacitors Cf1 and Cf2. The gain can therefore be switched with the use of the switches SW_cf1 and SW_cf2.

The switch SW_RST is a switch that resets electric charge accumulated in the feedback capacitors Cf1 and Cf2 of the integrating amplifier 201. Switching the switch SW_RST on makes a voltage at the ends of the feedback capacitor Cf1 and the ends of the feedback capacitor Cf2 equal to the reference voltage Vref, thereby resetting the electric charge.

The resistor $R_{LPF}$ connected to the output terminal of the integrating amplifier 201 functions, in combination with the sample-and-hold circuit SW_CDS1-$C_{SH1}$ and the sampleand-hold circuit SW_CDS2-$C_{SH2}$, which are connected downstream of the resistor $R_{LPF}$, as a low pass filter for reducing output noise of the integrating amplifier 201. The resistor $R_{LPF}$ is a variable resistor that has a resistance value selected by a control signal from among prepared resistance values.

The sample-and-hold circuit SW_CDS1-$C_{SH1}$ and the sample-and-hold circuit SW_CDS2-$C_{SH2}$, which are connected downstream of the resistor $R_{LPF}$, are sample-and-hold circuits for correlated double sampling (CDS). The switch SW_CDS1 and the capacitor $C_{SH1}$ sample a noise signal after the integrating amplifier 201 is reset. The switch SW_CDS2 and the capacitor $C_{SH2}$ sample a signal of the integrating amplifier 201 after a signal from a pixel is transferred, namely, a pixel signal. The noise signal and the pixel signal receive differential processing in the sample-and-hold amplifier 116 in FIG. 1 to be output to the analog/digital converter 117. Performing the differential processing on the noise signal and the pixel signal in the sample-and-hold amplifier 116 removes low-frequency noise.

The control signals RST1 and RST2 in FIG. 1 are signals for controlling the switch SW_RST in FIG. 2. When the control signals RST1 and RST2 reach the high level, the switch SW_RST is switched on. When the control signals RST1 and RST2 reach the low level, the switch SW_RST is switched off. The control signals CDS1_1 and CDS1_2 in FIG. 1 are signals for controlling the switch SW_CDS1 in FIG. 2. When the control signals CDS1_1 and CDS1_2 reach the high level, the switch SW_CDS1 is switched on. When the control signals CDS1_1 and CDS1_2 reach the low level, the switch SW_CDS1 is switched off. The control signals CDS2_1 and CDS2_2 in FIG. 1 are signals for controlling the switch SW_CDS2 in FIG. 2. When the control signals CDS2_1 and CDS2_2 reach the high level, the switch SW_CDS2 is switched on. When the control signals CDS2_1 and CDS2_2 reach the low level, the switch SW_CDS2 is switched off. The control signals LPF1 and LPF2 in FIG. 1 are control signals for switching the resistance value of the resistor $R_{LPF}$ in FIG. 2, and each include a plurality of bits. The control signals CF1 and CF2 in FIG. 1 are signals for controlling the switching on/off of the switches SW_cf1 and SW_cf2 in FIG. 2, respectively, and each include a plurality of bits. When the control signal CF1 reaches the high level, the switch SW_cf1 is switched on. When the control signal CF1 reaches the low level, the switch SW_cf1 is switched off. When the control signal CF2 reaches the high level, the switch SW_cf2 is switched on. When the control signal CF2 reaches the low level, the switch SW_cf2 is switched off.

The controls signals Power1 and Power2 in FIG. 1 are signals for switching between an idling mode and a readout mode. When the control signals Power1 and Power2 reach the low level, a switch to the idling mode is made. When the control signals Power1 and Power2 reach the high level, a switch to the readout mode is made. In the idling mode, the current consumption of the column amplifiers 111 to 114 is controlled to reduce the power spent on the integrating amplifier 201 and the analog/digital converter 117, which do not execute a readout operation. In the readout mode, power consumption is increased so that the column amplifiers 111 to 114 are driven at a desired noise performance level and a desired speed. The column amplifiers 111 to 114 in the idling mode only have a driving ability enough to maintain the electric potential of the signal lines Sig1 to Sig4 and consume power that is ¼ or less of the power consumption in the readout mode.

The control signals RST1, CDS1_1, CDS2_1, LPF1, Power1, and CF1 are supplied to the column amplifiers 111 to 113. The control signals RST2, CDS1_2, CDS2_2, LPF2, Power2, and CF2 are supplied to the column amplifier 114. The operation of reading out the second conversion elements X1 to X3 and the operation of reading out the first conversion elements S11 to S33 can thus be executed independently of each other. In addition, values optimum for the operation of the first conversion elements S11 to S33 and values optimum for the operation of the second conversion elements X1 to X3 can be set separately from each other as the feedback capacitors Cf1 and Cf2 and the resistance value of the resistor $R_{LPF}$.

Figure 3:
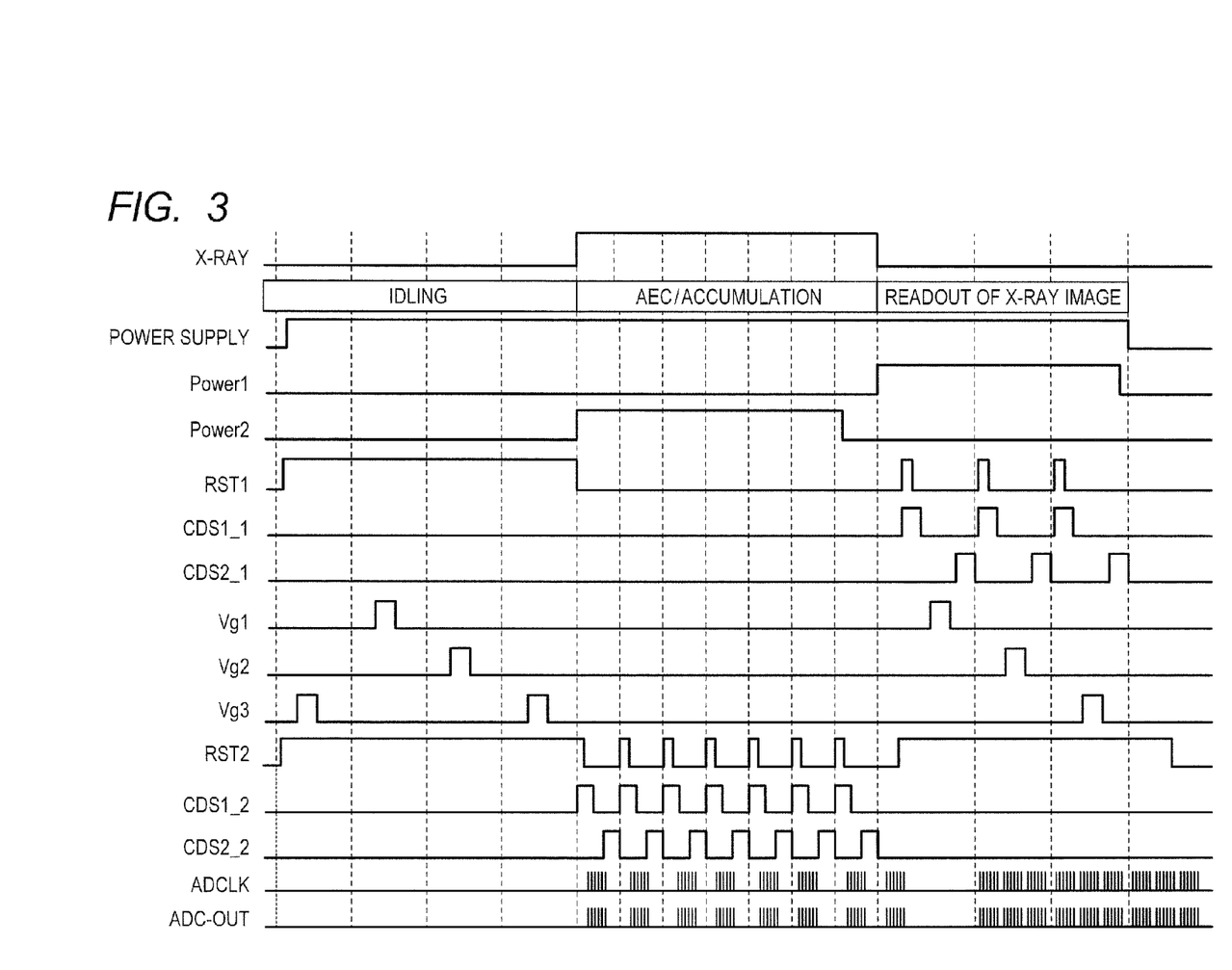
FIG. 3 is a timing chart for showing a method of driving the radiation imaging apparatus.

FIG. 3 is a timing chart for showing a driving method (AEC control method, "AEC control" means control by AEC) for the radiation imaging apparatus. The radiation imaging apparatus needs to execute three operations in order to obtain a radiographic image. A first operation is an idling operation. This operation is for stabilizing pixel characteristics after the area sensor 101 is powered on. The length of time required for this operation, though varies depending on the pixel characteristics, is approximately 10 seconds. For the duration of the idling operation, the TFT switches T11 to T33 are switched on by high-level pulses of the gate lines Vg1 to Vg3 to remove dark currents accumulated in the first conversion elements S11 to S33 and minimize the effect of the dark currents on the radiographic image. The power consumption of the readout circuit 104 is also minimized by putting the readout circuit 104 into the idling mode and thus reducing heat generation because image readout is not required for the duration. At this point, the integrating amplifier 201 may be reset by switching the switch SW_RST on in order to prevent an input offset current of the integrating amplifier 201 from causing the output of the integrating amplifier 201 to drift.

A second operation is an accumulation operation (AEC control operation) in which the gate lines Vg1 to Vg3 are set to the low level to switch off all of the TFT switches T11 to T33 and accumulate electric charge generated by X-ray irradiation in the conversion elements S11 to S33 and X1 to X3. The transition from the first operation to the second operation is synchronized with the press of an X-ray exposure button. When an operator presses the exposure button, the on/off operation of the TFT switches T11 to T13 in the idling operation is ended and the transition to the accumulation operation is executed. During the accumulation operation, where the gate lines Vg1 to Vg3 are at the low level and the TFT switches T11 to T33 are switched off, the first conversion elements S11 to S33 cannot determine whether or not an X-ray has reached the radiation imaging apparatus. The dose of X-ray irradiation is therefore monitored by reading out signals from the second conversion elements X1 to X3 with the column amplifier 114.

In the operation of reading out signals of the second conversion elements X1 to X3, the column amplifier 114 first switches the switch SW_RST on with the use of the control signal RST2, and resets the integrating amplifier 201 to remove previous signals. Thereafter, the control signal CDS1_2 is used to switch the switch SW_CDS1 on, and a noise signal is sampled and written in the capacitor $C_{SH1}$. The control signal CDS2_2 is then used to switch the switch SW_CDS2 on, and integral values of signals output from the second conversion elements X1 to X3 are sampled and held in the capacitor $C_{SH2}$.

Thereafter, the sample-and-hold amplifier 116 outputs a differential signal of a signal in the capacitor $C_{SH1}$ and a signal in the capacitor $C_{SH2}$ to the analog/digital converter 117. The analog/digital converter 117 converts the output signal of the sample-and-hold amplifier 116 from an analog value into a digital value. A signal processing unit 106 integrates the digital value output from the analog/digital converter 117, thereby determining the amount of X-ray irradiation on the area sensor 101.

The demanded response speed of AEC control is 100 μs, which is in no way fulfilled if signals of the conversion elements S11 to S33 are all read out by the column amplifiers 111 to 113. This embodiment can cut short the length of time from the sample-and-hold to the outputting of the digital value by reading out only signals of the second conversion elements X1 to X3, with the use of the column amplifier 114. In the case where the analog/digital converter 117 that is large in bit value and high in definition is used, the processing time and data transfer time of the analog/digital converter 117 are long, and reducing the number of pieces of data to receive analog/digital conversion is therefore effective in improving the speed of AEC control.

The second conversion elements X1 to X3 are connected directly to the signal line Sig4 without an intervening TFT switch. Accordingly, a current is constantly output to the column amplifier 114 in an amount corresponding to the X-ray dose, with the result that signals in a high level period of the control signal RST2 and a high level period of the control signal CDS1_2 are lost. The high level periods of the control signal RST2 and the control signal CDS1_2 may thus be cut short.

When it is determined that the integrated quantity of signals read out by the column amplifier 114 corresponds to the desired X-ray dose, the control circuit 105 and the signal processing unit 106 instruct a radiation generating apparatus 509 (FIG. 5) to stop X-ray irradiation, and execute an X-ray image readout operation, which is a third operation. The determination may be made by a control system 505 (FIG. 5) instead. The X-ray image readout operation involves reading out electric charge that are accumulated in the first conversion elements S11 to S33 with the use of the column amplifiers 111 to 113.

In the operation of reading out signals of the first conversion elements S11 to S33, the column amplifiers 111 to 113 first switch the switch SW_RST on with the use of the control signal RST1, and reset the integrating amplifier 201 to remove previous signals. Thereafter, the control signal CDS1_1 is used to switch the switch SW_CDS1 on, and a noise signal is sampled and written in the capacitor $C_{SH1}$. The gate line Vg1 subsequently reaches the high level, thereby switching the TFT switches T11, T12, and T13 on, and signals of the first conversion elements S11, S12, and S13 are output to the signal lines Sig1, Sig2, and Sig3, respectively. The control signal CDS1_2 is then used to switch the switch SW_CDS2 on, and integral values of signals output from the first conversion elements S11, S12, and S13 are sampled and held in the capacitor $C_{SH2}$. Thereafter, the multiplexer 115 outputs signals of the first conversion elements S11, S12, and S13 to the sample-and-hold amplifier 116 in time series. The sample-and-hold amplifier 116 then outputs a differential signal of a signal in the capacitor $C_{SH1}$ and a signal in the capacitor $C_{SH2}$ to the analog/digital converter 117. The analog/digital converter 117 converts the output signal of the sample-and-hold amplifier 116 from an analog value to a digital value.

The column amplifiers 111 to 113 again switch the switch SW_RST on with the use of the control signal RST1, and reset the integrating amplifier 201 to remove previous signals. Thereafter, the control signal CDS1_1 is used to switch the switch SW_CDS1 on, and a noise signal is sampled and written in the capacitor $C_{SH1}$. The gate line Vg2 subsequently reaches the high level, thereby switching the TFT switches T21, T22, and T23 on, and signals of the first conversion elements S21, S22, and S23 are output to the signal lines Sig1, Sig2, and Sig3, respectively. The control signal CDS1_2 is then used to switch the switch SW_CDS2 on, and integral values of signals output from the first conversion elements S21, S22, and S23 are sampled and held in the capacitor $C_{SH2}$. Thereafter, the multiplexer 115 outputs signals of the first conversion elements S21, S22, and S23 to the sample-and-hold amplifier 116 in time series. The sample-and-hold amplifier 116 then outputs a differential signal of a signal in the capacitor $C_{SH1}$ and a signal in the capacitor $C_{SH2}$ to the analog/digital converter 117. The analog/digital converter 117 converts the output signal of the sample-and-hold amplifier 116 from an analog value to a digital value.

The column amplifiers 111 to 113 again switch the switch SW_RST on with the use of the control signal RST1, and reset the integrating amplifier 201 to remove previous signals. Thereafter, the control signal CDS1_1 is used to switch the switch SW_CDS1 on, and a noise signal is sampled and written in the capacitor $C_{SH1}$. The gate line Vg3 subsequently reaches the high level, thereby switching the TFT switches T31, T32, and T33 on, and signals of the first conversion elements S31, S32, and S33 are output to the signal lines Sig1, Sig2, and Sig3, respectively. The control signal CDS1_2 is then used to switch the switch SW_CDS2 on, and integral values of signals output from the first conversion elements S31, S32, and S33 are sampled and held in the capacitor $C_{SH2}$. Thereafter, the multiplexer 115 outputs signals of the first conversion elements S31, S32, and S33 to the sample-and-hold amplifier 116 in time series. The sample-and-hold amplifier 116 then outputs a differential signal of a signal in the capacitor $C_{SH1}$ and a signal in the capacitor $C_{SH2}$ to the analog/digital converter 117. The analog/digital converter 117 converts the output signal of the sample-and-hold amplifier 116 from an analog value to a digital value.

The column amplifier 114 in the X-ray image readout operation executes a reset operation in which the electric potential of the signal line Sig4 is steadied firmly in order to prevent the electric potential of the signal line Sig4 from fluctuating during the operation of reading out the first conversion elements S11 to S33 and consequently affecting image quality. After the transition to the accumulation operation, an image that is not irradiated with an X-ray may be read out to be used for a correction of the X-ray image.

As described above, the control circuit 105 can control the column amplifier 114 independently of control exerted over the column amplifiers 111 to 113. An X-ray image readout period in which the column amplifiers 111 to 113 output voltages corresponding to electric charge of the first conversion elements S11 to S33 differs from an AEC control period in which the column amplifier 114 outputs a voltage corresponding to electric charge of the second conversion elements X1 to X3. The multiplexer 115 selects and outputs the output voltage of the column amplifier 114 in the AEC control period (a first period) and, in the X-ray image readout period (a second period), selects and outputs the output voltages of the plurality of column amplifiers 111 to 113. In the AEC control period where the radiation imaging apparatus receives irradiation of a radiation ray (X-ray), the column amplifier 114 outputs a voltage corresponding to electric charge of the second conversion elements X1 to X3, and the column amplifiers 111 to 113 do not output voltages corresponding to electric charge of the first conversion elements S11 to S33. The column amplifiers 111 to 113 and the column amplifier 114 are controlled differently from each other in at least one aspect out of power consumption, gain, sample-and-hold operation, reset operation, and low pass filter.

Figure 4:
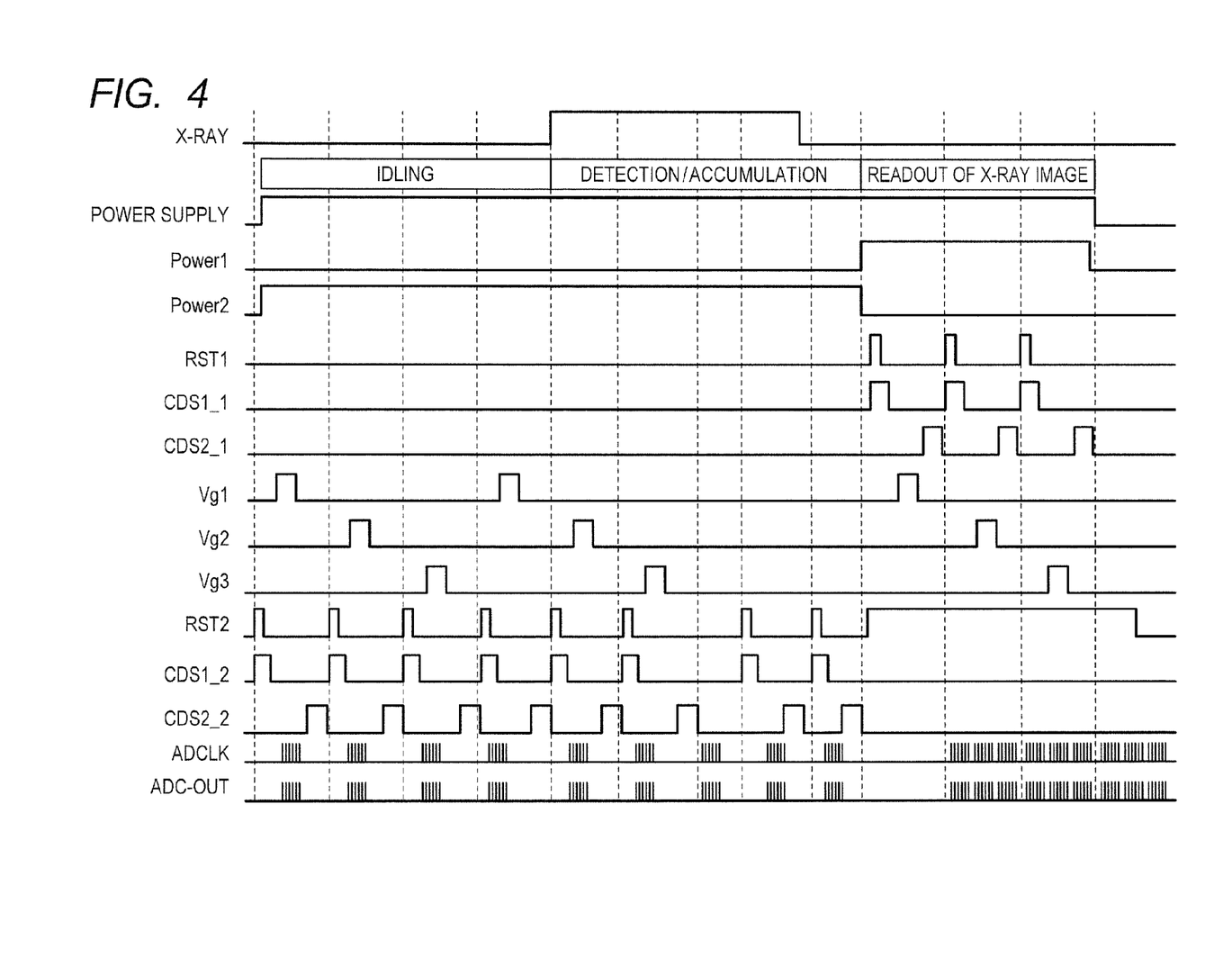
FIG. 4 is a diagram for showing an example of X-ray irradiation detection.

FIG. 4 is a timing chart for showing another driving method (X-ray detecting operation) for the radiation imaging apparatus according to the first embodiment of the present invention. The radiation imaging apparatus needs to execute three operations in order to obtain an X-ray image as well as the operations in FIG. 3. A first operation is an idling operation. This operation is for stabilizing pixel characteristics after the radiation imaging apparatus is powered on. The length of time required for this operation, though varies depending on the pixel characteristics, is approximately 10 seconds. For the duration of the idling operation, the TFT switches T11 to T33 are switched on/off by pulses of the gate lines Vg1 to Vg3 to remove dark currents accumulated in the first conversion elements S11 to S33 and minimize the effect of the dark currents on the X-ray image.

The power mode of the column amplifier 114 at this point is set to the readout mode with the use of the control signal Power2 to keep detecting signals of the second conversion elements X1 to X3. The operation of reading out signals of the second conversion elements X1 to X3 is executed by coordinating the resetting of the integrating amplifier 201 via the control signal RST2 and the sample-and-hold via the control signals CDS1_2 and CDS2_2 with pulses of the gate lines Vg1 to Vg3. The reason therefor is described below. The gate lines Vg1 to Vg3 and the signal lines Sig1 to Sig3 are coupled by an existing capacitor, and the signal lines Sig1 to Sig3 and the line of the bias voltage Vs are coupled by an existing capacitor. Therefore, the resetting and the sample-and-hold are coordinated with the pulses of the gate lines Vg1 to Vg3 in order to prevent the operation of the gate lines Vg1 to Vg3 from fluctuating the electric potential of the signal line Sig4 and consequently causing an error when the second conversion elements X1 to X3 are read out.

At this point, image readout is not required and the power consumption of the column amplifiers 111 to 113 is therefore minimized by putting the column amplifiers 111 to 113 into a low power consumption mode with the use of the control signal Power1 and thus reducing heat generation. The integrating amplifier 201 may be reset in order to prevent the input offset current of the integrating amplifier 201 from causing the output of the integrating amplifier 201 to drift.

A second operation is an accumulation operation (detection operation). Signals of the second conversion elements X1 to X3 are monitored and, when the signal processing unit 106 determines that a preset threshold has been exceeded, the gate lines Vg1 to Vg3 are fixed to the low level to switch off all of the TFT switches T11 to T33. The radiation imaging apparatus thus shifts from the first operation to the second operation, which is the operation of accumulating electric charge that are generated in the first conversion elements S11 to S33.

During the accumulation operation, the TFT switches T11 to T33 are switched off and other column amplifiers than the column amplifier 114 connected to the second conversion elements X1 to X3, specifically, the column amplifiers 111 to 113, are put into the idling mode with the use of the control signal Power1 in order to reduce power consumption.

The column amplifier 114 connected to the second conversion elements X1 to X3 keeps reading out signals during X-ray irradiation as well as the operation in FIG. 3 and continues the readout operation until the end of X-ray irradiation is detected. From the signals obtained through this operation, the control circuit 105 and the signal processing unit 106 determine that X-ray irradiation has been completed, and then execute an X-ray image readout operation, which is a third operation. The determination may be made by the control system 505 (FIG. 5) instead.

The X-ray image readout operation involves reading out electric charge that are accumulated in the first conversion elements S11 to S33 with the use of the column amplifiers 111 to 113. In the X-ray image readout operation, the column amplifiers 111 to 113 first reset the integrating amplifier 201 with the use of the high level pulse of the control signal RST1. Immediately after the resetting, the control signal CDS1_1 is set to the high level to start the sampling of the noise signal out of signals of the integrating amplifier 201. The sampling is completed when a desired time elapses after the completion of the resetting of the integrating amplifier 201. The gate driver 102 subsequently outputs a gate pulse to the gate line Vg1 to switch on the TFT switches T11, T12, and T13 in the first row, and electric charge accumulated in the first conversion elements S11, S12, and S13 are transferred to the column amplifiers 111 to 113. After the TFT switches T11, T12, and T13 are kept on for a desired length of time, the TFT switches T11, T12, and T13 are switched off. Next, the control signal CDS2_1 is set to the high level to start the sampling of a pixel signal (image signal) out of signals of the integrating amplifier 201. After a desired length of time elapses, the control signal CDS2_1 is set to the low level to end the sampling. Thereafter, the multiplexer 115 outputs signals of the first conversion elements S11, S12, and S13 to the sample-and-hold amplifier 116 in time series. The sample-and-hold amplifier 116 then outputs a differential signal of a signal in the capacitor $C_{SH1}$ and a signal in the capacitor $C_{SH2}$ to the analog/digital converter 117. The analog/digital converter 117 converts the output signal of the sample-and-hold amplifier 116 from an analog value into a digital value.

The integrating amplifier 201 is reset again with the use of the high level pulse of the control signal RST1. Immediately after the resetting, the control signal CDS1_1 is set to the high level to start the sampling of a noise signal out of signals of the integrating amplifier 201. The sampling is completed when a desired time elapses after the completion of the resetting of the integrating amplifier 201. The gate driver 102 subsequently outputs a gate pulse to the gate line Vg2 to switch on the TFT switches T21, T22, and T23 in the second row, and electric charge accumulated in the first conversion elements S21, S22, and S23 are transferred to the column amplifiers 111 to 113. After the TFT switches T21, T22, and T23 are kept on for a desired length of time, the TFT switches T21, T22, and T23 are switched off. Next, the control signal CDS2_1 is set to the high level to start the sampling of a pixel signal out of signals of the integrating amplifier 201. After a desired length of time elapses, the control signal CDS2_1 is set to the low level to end the sampling. Thereafter, the multiplexer 115 outputs signals of the first conversion elements S21, S22, and S23 to the sample-and-hold amplifier 116 in time series. The sample-and-hold amplifier 116 then outputs a differential signal of a signal in the capacitor $C_{SH1}$ and a signal in the capacitor $C_{SH2}$ to the analog/digital converter 117. The analog/digital converter 117 converts the output signal of the sample-and-hold amplifier 116 from an analog value into a digital value.

The integrating amplifier 201 is reset again with the use of the high level pulse of the control signal RST1. Immediately after the resetting, the control signal CDS1_1 is set to the high level to start the sampling of a noise signal out of signals of the integrating amplifier 201. The sampling is completed when a desired time elapses after the completion of the resetting of the integrating amplifier 201. The gate driver 102 subsequently outputs a gate pulse to the gate line Vg3 to switch on the TFT switches T31, T32, and T33 in the third row, and electric charge accumulated in the first conversion elements S31, S32, and S33 are transferred to the column amplifiers 111 to 113. After the TFT switches T31, T32, and T33 are kept on for a desired length of time, the TFT switches T31, T32, and T33 are switched off. Next, the control signal CDS2_1 is set to the high level to start the sampling of a pixel signal out of signals of the integrating amplifier 201. After a desired length of time elapses, the control signal CDS2_1 is set to the low level to end the sampling. Thereafter, the multiplexer 115 outputs signals of the first conversion elements S31, S32, and S33 to the sample-and-hold amplifier 116 in time series. The sample-and-hold amplifier 116 then outputs a differential signal of a signal in the capacitor $C_{SH1}$ and a signal in the capacitor $C_{SH2}$ to the analog/digital converter 117. The analog/digital converter 117 converts the output signal of the sample-and-hold amplifier 116 from an analog value into a digital value.

As described above, an X-ray image readout period in which the column amplifiers 111 to 113 output voltages corresponding to electric charge of the first conversion elements S11 to S33 differs from an idling period and detection period in which the column amplifier 114 outputs a voltage corresponding to electric charge of the second conversion elements X1 to X3. The multiplexer 115 selects and outputs the output voltage of the column amplifier 114 in the idling period and the detection period (a first period) and, in the X-ray image readout period (a second period), selects and outputs the output voltages of the column amplifiers 111 to 113. In the idling period until the radiation imaging apparatus receives irradiation of a radiation ray (X-ray), the column amplifier 114 outputs a voltage corresponding to electric charge of the second conversion elements X1 to X3, and the column amplifiers 111 to 113 do not output voltages corresponding to electric charge of the first conversion elements S11 to S33.

Power consumption can be reduced in this embodiment by setting only the power mode of the column amplifier 114 to the readout mode in the idling operation with the use of the control signal Power2, whereas the column amplifiers 111 to 113 are put into the idling mode with the use of the control signal Power1. The shortening of the drive time due to heat generation or low battery can thus be prevented even when it takes long to photograph. In addition, because the column amplifier 114 alone reads out signals of the second conversion elements X1 to X3, X-ray irradiation is detected in a short time and the amount of unnecessary X-ray exposure can be reduced.

The second conversion elements X1 to X3 are connected directly to the signal line Sig4 without an intervening TFT switch, as in the configuration described above. Accordingly, a current is constantly output to the column amplifier 114 in an amount corresponding to the X-ray dose, with the result that signals in a high level period of the control signal RST2 and a high level period of the control signal CDS1_2 are lost. The high level periods of the control signal RST2 and the control signal CDS1_2 may thus be cut short.

The column amplifier 114 in the X-ray image readout operation executes a reset operation in which the electric potential of the signal line Sig4 is steadied firmly in order to prevent the electric potential of the signal line Sig4 from fluctuating during the operation of reading out the first conversion elements S11 to S33 and consequently affecting image quality. After the transition to the accumulation operation, an image that is not irradiated with an X-ray may be read out to be used for a correction of the X-ray image.

While the radiation imaging apparatus described in this embodiment has the conversion elements S11 to S33 and X1 to X3 for 4×3 pixels, the present invention is not limited to this pixel count. One row of second conversion elements X of radiation detecting pixels per a hundred rows or per five hundred rows is sufficient, and the number of column amplifiers 114 connected to the second conversion elements X of the radiation detecting pixels, which are in operation during idling, is accordingly 1% to 0.2% of the total line count. Power consumed during idling can thus be reduced.

Second Embodiment

Figure 5:
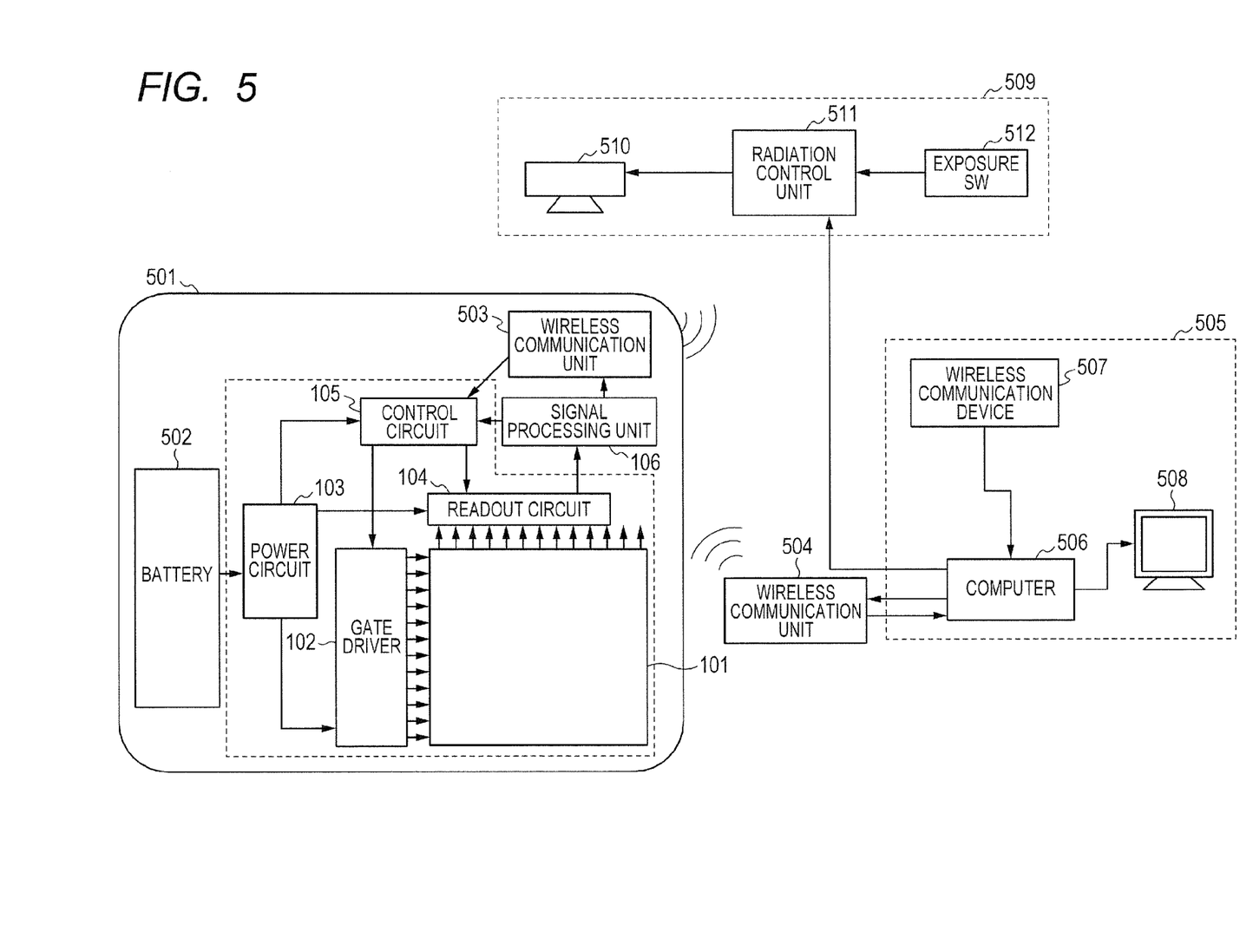
FIG. 5 is a diagram for illustrating a configuration example of a radiation imaging system.

FIG. 5 is a diagram for illustrating a configuration example of a radiation imaging system according to a second embodiment of the present invention. The radiation imaging system of this embodiment includes, in addition to the radiation imaging apparatus 501 of the first embodiment, a wireless communication unit 504, the control system 505, and the radiation generating apparatus 509. The radiation imaging apparatus 501 includes the area sensor 101, the gate driver 102, the power circuit 103, the readout circuit 104, the control circuit 105, and the signal processing unit 106 as in FIG. 1, and further includes a battery 502 and a wireless communication unit 503. The battery 502 supplies a supply voltage to the power circuit 103. The control circuit 105 and the signal processing unit 106 hold communication to and from the wireless communication unit 504 via the wireless communication unit 503.

The control system 505 includes a computer 506, a wireless communication device 507, and a display 508 to control the radiation imaging apparatus 501 and the radiation generating apparatus 509. The computer 506 holds wireless communication to and from the radiation imaging apparatus 501 via the wireless communication unit 504. The radiation generating apparatus 509 includes a radiation source (radiation tube) 510, a radiation control unit 511, and an exposure switch 512 to irradiate the radiation imaging apparatus 501 with a radiation ray through a subject.

The wireless communication unit 503 is a wireless communication unit for the radiation imaging apparatus 501. The wireless communication unit 504 is a wireless communication unit for the control system 505. The wireless communication units 503 and 504 are capable of transmitting, by radio, signals of radiation ray irradiation, signals for synchronizing one event with another, image signals of the radiation imaging apparatus 501, signals for AEC control, signals for X-ray irradiation detection, and control signals for controlling the driving of the area sensor 101.

The radiation imaging apparatus 501 uses the readout circuit 104 of the first embodiment, and is accordingly capable of AEC control and X-ray irradiation detection without decreasing the length of a drive time in which the radiation imaging apparatus 501 is driven on the battery 502.

Third Embodiment

Figure 6:
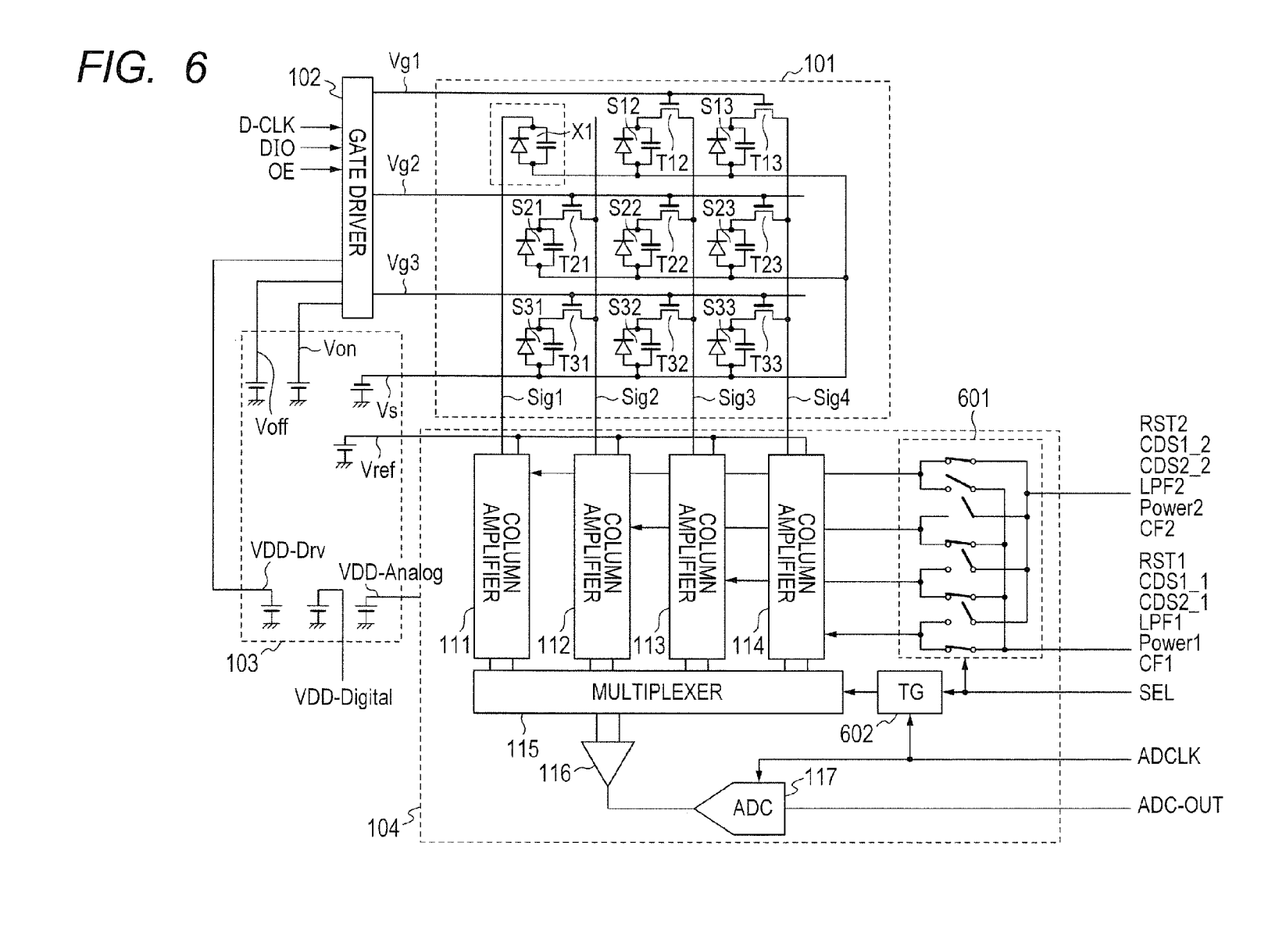
FIG. 6 is a diagram for illustrating a configuration example of another radiation imaging apparatus.

FIG. 6 is a diagram for illustrating a configuration example of a radiation imaging apparatus according to a third embodiment of the present invention. This embodiment (FIG. 6) is obtained by adding a switching unit 601 and a timing generator 602 to the first embodiment (FIG. 1).

Differences of this embodiment from the first embodiment are described below.

The second conversion element X1 of the radiation detecting pixels is connected to the column amplifier 111 via the signal line Sig1. The first conversion elements S21 and S31 of the image pixels are connected to the column amplifier 112 via the signal line Sig2. The first conversion elements S12, S22, and S32 of the image pixels are connected to the column amplifier 113 via the signal line Sig3. The first conversion elements S13, S23, and S33 of the image pixels are connected to the column amplifier 114 via the signal line Sig4.

The switching unit 601 supplies the column amplifiers 111 to 114 with the control signals RST1, CDS1_1, CDS2_1, LPF1, Power1, and CF1, or the control signals RST2, CDS1_2, CDS2_2, LPF2, Power2, and CF2, depending on the value of a signal SEL. The switching unit 601 is capable of switching signals to be supplied to the column amplifiers 111 to 114 between the same control signals and different control signals.

The timing generator 602 controls the multiplexer 115 in a manner determined by the signal SEL. Depending on the value of the signal SEL, the multiplexer 115 selects only the column amplifier 111 to which the control signals RST2, CDS1_2, CDS2_2, LPF2, Power2, and CF2 are supplied, or only the column amplifiers 112 to 114 to which the control signals RST1, CDS1_1, CDS2_1, LPF1, Power1, and CF1 are supplied. In the case where the column amplifier 111 is fixed as a column amplifier that reads out the second conversion element X1, the signal line Sig1, which connects the second conversion element X1 to the column amplifier 111, may intersect with the other signal lines, Sig2 to Sig4, due to how the signal line Sig1 is laid out, thereby putting limitations on the placement of the second conversion element X1.

According to this embodiment, the degree of freedom in the placement of the second conversion element X1 is increased and the second conversion element X1 can be put in a more effective place. For example, the second conversion element X1 in FIG. 6 can be disposed in a place where the first conversion element S11 in FIG. 1 is located. The second conversion elements of the plurality of radiation detecting pixels may be dispersed throughout the area sensor 101. In this case also, there is no need to align the radiation detecting pixels with the positions of the column amplifiers to which the radiation detecting pixels are connected, and the radiation detecting pixels can be put in arbitrary places.

Fourth Embodiment

Figure 7:
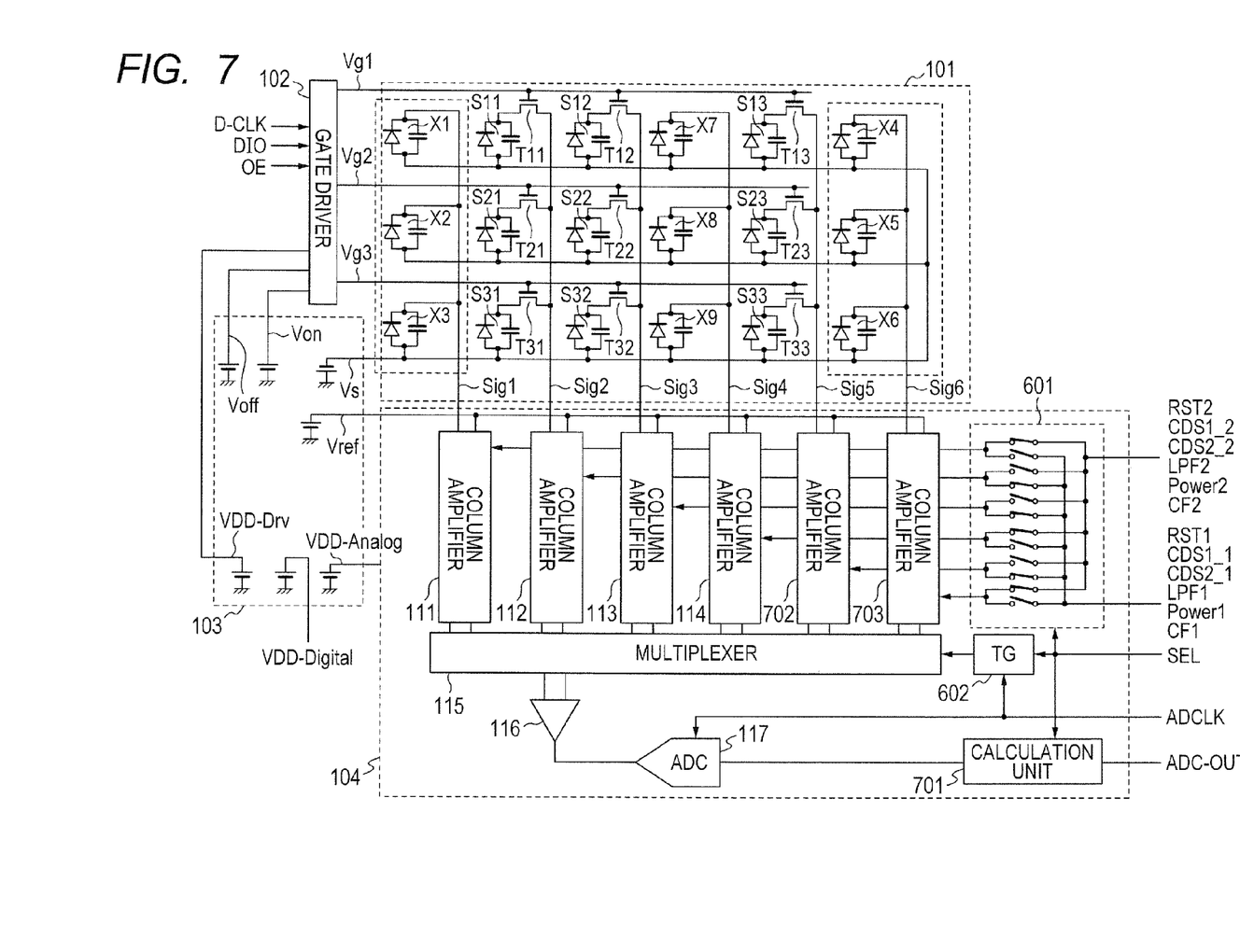
FIG. 7 is a diagram for illustrating a configuration example of still another radiation imaging apparatus.

FIG. 7 is a diagram for illustrating a configuration example of a radiation imaging apparatus according to a fourth embodiment of the present invention. This embodiment (FIG. 7) is obtained by adding a calculation unit 701, column amplifiers 702 and 703, conversion elements X2 to X9, the conversion element S11, and the TFT switch T11 to the third embodiment (FIG. 6). The conversion elements X2 to X9 and S11 convert a radiation ray into electric charge. The conversion elements X1 to X9 are included in a plurality of radiation detecting pixels for detecting radiation irradiation. The first conversion elements S11 to S33 and the TFT switches T11 to T33 are included in a plurality of image pixels for obtaining a radiographic image. The conversion elements X1 to X9 convert a radiation ray into electric charge in order to detect radiation irradiation. The first conversion elements S11 to S33 convert a radiation ray into electric charge in order to obtain a radiographic image.

Differences of this embodiment from the third embodiment are described below.

The conversion elements X1 to X3 are connected to the column amplifier 111 via the signal line Sig1. The conversion elements S11, S21, and S31 are connected to the column amplifier 112 via the TFT switches T11, T21, and T31 and the signal line Sig2. The conversion elements S12, S22, and S32 are connected to the column amplifier 113 via the TFT switches T12, T22, and T32 and the signal line Sig3. The conversion elements X7 to X9 are connected to the column amplifier 114 via the signal line Sig4. The conversion elements S13, S23, and S33 are connected to the column amplifier 702 via the TFT switches T13, T23, and T33 and a signal line Sig5. The conversion elements X4 to X6 are connected to the column amplifier 703 via a signal line Sig6.

The column amplifiers 112, 113, and 702, which are first column amplifiers, are connected to the first conversion elements S11 to S33 via the TFT switches T11 to T33 to output voltages corresponding to electric charge of the first conversion elements S11 to S33. The column amplifier 111, which is a second column amplifier, is connected directly to the second conversion elements X1 to X3 to output a voltage corresponding to electric charge of the second conversion elements X1 to X3. The column amplifier 114, which is a third column amplifier, is connected directly to the conversion elements X7 to X9, which are third conversion elements, to output a voltage corresponding to electric charge of the third conversion elements X7 to X9. The column amplifier 703, which is a fourth column amplifier, is connected directly to the conversion elements X4 to X6, which are fourth conversion elements, to output a voltage corresponding to electric charge of the fourth conversion elements X4 to X6.

The switching unit 601 supplies the control signals RST1, CDS1_1, CDS2_1, LPF1, Power1, and CF1 to the column amplifiers 112, 113, and 702. The switching unit 601 also supplies the control signals RST2, CDS1_2, CDS2_2, LPF2, Power2, and CF2 to the column amplifiers 111, 114, and 703.

The calculation unit 701 has a memory for a plurality of pixels, is capable of holding a digital value that is output from the analog/digital converter 117, and is capable of calculation that uses the held value. The calculation unit 701 also has a processor, and is capable of performing various types of calculation such as addition, subtraction, multiplication, and division, depending on the value of the signal SEL.

For example, the calculation unit 701 can output the result of addition that adds only signals based on output voltages of the column amplifiers 111, 114, and 703, which are connected to the conversion elements X1 to X9. This processing can improve the sensitivity of X-ray dose detection.

The calculation unit 701 obtains (by subtraction) differentials between signals of the column amplifiers 111, 114, and 703, which are connected to the conversion elements X1 to X9, and signals of the column amplifiers 112, 113, and 702, which are connected to the first conversion elements S11 to S33. Common mode noise that is common to the column amplifiers can thus be removed. This processing can improve the signal-to-noise ratio (SN ratio) in X-ray dose detection, and accordingly improve the accuracy of the detection.

The calculation unit 701 is also capable of averaging processing by addition and division. The conversion elements X1 to X9 are disposed within the plane of the area sensor 101 in order to accurately measure the amount of radiation irradiation on the area sensor 101. It is not always necessary to read out all signals of the conversion elements X1 to X9 independently of one another. For example, in the case where only the fact that the radiation imaging apparatus has received irradiation of an X-ray is to be detected, the calculation unit 701 may detect X-ray irradiation by the averaging of signals of the column amplifiers 111, 114, and 703, which are connected to the conversion elements X1 to X9.

If the averaging is to be performed by the signal processing unit 106 (FIG. 1), data needs to be transferred and the additional time required for the data transfer is a waste. Performing the averaging with the calculation unit 701 can therefore cut short the time required to output data even more, and improve the response speed of X-ray dose detection.

As described above, column amplifiers that are connected to the conversion element X1 and other conversion elements X and column amplifiers that are connected to the first conversion elements S11 to S33 execute different operations in the first embodiment to the fourth embodiment. In X-ray dose detection, only the column amplifiers that are connected to the conversion element X1 and other conversion elements X, which are radiation detecting pixels, are allowed to read out, to thereby cut short the length of time from the sampling of a pixel signal to data output.

The radiation imaging apparatus is also capable of detecting the start of X-ray irradiation and the irradiation amount while reducing the overall power consumption of the radiation imaging apparatus, by increasing the power consumption of only the column amplifiers that are connected to the conversion element X1 and other conversion elements X, which are radiation detecting pixels, and improving the SN ratio in X-ray dose detection.

Other Embodiments

Embodiments of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiments and/or that includes one or more circuits (e.g., application specific integrated circuit (ASIC)) for performing the functions of one or more of the above-described embodiments, and by a method performed by the computer of the system or apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-146763, filed Jul. 17, 2014 which is hereby incorporated by reference herein in its entirety.

What is claimed is:

1. A radiation imaging apparatus, comprising:
    a first conversion element arranged to convert a radiation ray into electric charge in order to obtain a radiographic image;
    a first amplifier arranged to output a voltage corresponding to the electric charge of the first conversion element;
    a second conversion element arranged to convert the radiation ray into electric charge in order to detect radiation irradiation;
    a second amplifier arranged to output a voltage corresponding to the electric charge of the second conversion element; and
    a control circuit configured to control the first amplifier and the second amplifier,
    wherein the control circuit is capable of controlling the second amplifier independently of control that is exerted over the first amplifier.

2. A radiation imaging apparatus according to claim 1, wherein a period in which the first amplifier outputs the voltage corresponding to the electric charge of the first conversion element differs from a period in which the second amplifier outputs the voltage corresponding to the electric charge of the second conversion element.

3. A radiation imaging apparatus according to claim 1,
    wherein the first conversion element comprises a plurality of the first conversion elements, and the plurality of the first conversion elements are arranged in a matrix pattern,
    wherein the first amplifier comprises a plurality of the first amplifiers, and the plurality of the first amplifiers are arranged side by side in a row direction so as to be connected to the plurality of the first conversion elements, which are aligned in a column direction, and
    wherein the radiation imaging apparatus further comprises a multiplexer configured to select and output the output voltage of the second amplifier in a first period and to select and output the output voltages of the plurality of the first amplifiers in a second period.

4. A radiation imaging apparatus according to claim 1, wherein, during a period in which the radiation imaging apparatus receives irradiation of the radiation ray, the second amplifier outputs the voltage corresponding to the electric charge of the second conversion element, and the first amplifier is inhibited from outputting the voltage corresponding to the electric charge of the first conversion element.

5. A radiation imaging apparatus according to claim 1, wherein, during a period until the radiation imaging apparatus receives irradiation of the radiation ray, the second amplifier outputs the voltage corresponding to the electric charge of the second conversion element, and the first amplifier is inhibited from outputting the voltage corresponding to the electric charge of the first conversion element.

6. A radiation imaging apparatus according to claim 1, further comprising a switching unit, which is capable of switching signals to be supplied to the first amplifier and the second amplifier between the same control signals and different control signals.

7. A radiation imaging apparatus according to claim 1, further comprising:
   a third conversion element arranged to convert the radiation ray into electric charge in order to detect the radiation irradiation;
   a third amplifier arranged to output a voltage corresponding to the electric charge of the third conversion element; and
   a calculation unit configured to perform calculation by using a signal that is based on the output voltage of the second amplifier and a signal that is based on the output voltage of the third amplifier.

8. A radiation imaging apparatus according to claim 1, wherein the first amplifier and the second amplifier are controlled differently from each other in at least one aspect out of power consumption, gain, sample-and-hold operation, reset operation, and low pass filter.

9. A radiation imaging system, comprising:
   a radiation imaging apparatus including:
      a first conversion element arranged to convert a radiation ray into electric charge in order to obtain a radiographic image;
      a first amplifier arranged to output a voltage corresponding to the electric charge of the first conversion element;
      a second conversion element arranged to convert the radiation ray into electric charge in order to detect radiation irradiation;
      a second amplifier arranged to output a voltage corresponding to the electric charge of the second conversion element; and
      a control circuit configured to control the first amplifier and the second amplifier,
      wherein the control circuit is capable of controlling the second amplifier independently of control that is exerted over the first amplifier; and
   a radiation generating apparatus arranged to irradiate with the radiation ray.

* * * * *